United States Patent [19]

Winkler

[11] Patent Number: 5,555,618
[45] Date of Patent: Sep. 17, 1996

[54] METHOD OF MAKING ELECTRODE-CARRYING CATHETER

[75] Inventor: Josef Winkler, Reading, Pa.

[73] Assignee: Arrow International Investment Corp., Wilmington, Del.

[21] Appl. No.: 355,663

[22] Filed: Dec. 14, 1994

Related U.S. Application Data

[63] Continuation-in-part of Ser. No. 135,152, Oct. 12, 1993.
[51] Int. Cl.⁶ .................................................. H01R 43/00
[52] U.S. Cl. ............................... 29/825; 128/642; 606/48
[58] Field of Search ............................ 29/825; 156/169, 156/172; 128/642; 606/48

[56] References Cited

U.S. PATENT DOCUMENTS

| | | | |
|---|---|---|---|
| 4,934,049 | 6/1990 | Kiekhafer et al. | 29/825 X |
| 5,042,143 | 8/1991 | Holleman et al. | 29/825 |
| 5,347,708 | 9/1994 | Bisehoff et al. | 29/825 |
| 5,465,717 | 11/1995 | Imran et al. | . |
| 5,473,812 | 12/1995 | Morris et al. | 29/825 |

Primary Examiner—Carl J. Arbes
Attorney, Agent, or Firm—Amster, Rothstein & Ebenstein

[57] ABSTRACT

An electrode-carrying catheter has elongate, flexible tubing defining a proximal end, a distal end, and an electrically insulative outer tubular layer intermediate the ends, the tubing including a flexible core and a flexible non-conductive core-covering layer of plastic about the core. A plurality of electrically conductive electrodes is disposed on the outer tubular layer. In order to conduct electrical signals between the proximal end and each of the electrodes, a longitudinally-spaced plurality of flexible electrically conductive wires are helically wound around and at least partially into the core-covering layer. The wound wires define a removed section beneath a segment of each of the electrodes to enable electrical contact between a respective one of the wound wires and a respective one of the electrodes. Each electrode is in the form of an electrically conductive flexible flat ribbon for providing electrical communication with a respective one of the wound wires. Each ribbon is electrically and physically joined to a respective one of the wound wires, and wrapped about and crimped onto the outer tubular layer.

16 Claims, 5 Drawing Sheets

METHOD OF MAKING ELECTRODE-CARRYING CATHETER

CROSS-REFERENCE TO RELATED APPLICATION

This is a continuation-in-part of U.S. Ser. No. 08/135,152, filed Oct. 12, 1993.

BACKGROUND OF THE INVENTION

The present invention relates to electrode-carrying catheters, and more particularly to an inexpensive and reliable electrode-carrying catheter and a method of making the same.

Electrode-carrying catheters are well known in the medical art and find diagnostic and therapeutic utility in a wide variety of different applications. For example, mapping catheters are used diagnostically to produce a wave function of the heart's electrical impulses so that a doctor can determine proper functioning or fault, and location of the fault, in the heart. Ablative catheters are used therapeutically to destroy tissue in the heart causing tachycardia, utilizing radio frequency current catheter ablation. Such catheters are also used for heart pacing purposes and for analgesia in various parts of the body. Depending upon the particular application for which the catheter is used, it may be desirable for the catheter to carry one or more side electrodes, one or more end electrodes, or a combination thereof. The use of a plurality of smaller electrodes rather than a single large electrode frequently enables superior electrical contact with the tissue, this being a highly desirable factor in connection with mapping catheters in particular.

Electrically conductive wires have never proven to be entirely satisfactory as the electrodes since a functional electrode requires a much larger surface area than can be provided by a flexible wire. Further, unless provisions are made to fix the wire relative to the catheter tubing, it is extremely difficult to ensure that the wire is held in place so as to assure a reliable electrical contact. While a wire could be held in place by use of an electrically conductive adhesive securing the wire to the tubing, it would be extremely difficult to create an electrode by applying an adhesive in a thin layer over a large surface area, as would be necessary to ensure that the electrode layer is flexible.

While a biocompatible conductive paint as an electrode has the advantage of being easily applied in an extremely thin layer to the tubing outer surface by printing techniques, so as to ensure flexibility thereof and cover the wire, there are other problems associated with such conductive paint. While the flexible, thin layer of conductive ink painted on the tubing outer surface forms a good "electrical" connection with the wire, the conductive paint does not form a reliable "physical" connection with the wire, as necessary to ensure that the passage of the catheter through the human body along the guidewire to the proposed working site does not to some degree remove, separate or abrade away the thin layer of conductive paint.

Typically electrode-carrying catheters are made by applying metal strips on the outer side and/or distal (front) surfaces of a flexible tubing of non-conductive plastic, each side strip acting as a side or ring electrode and each distal strip acting as an end electrode. The presence of the metal strips limits the natural flexibility of the tubing so that the catheter is not of high flexibility throughout its entire length, and this presents problems in threading the catheter into the human body over a guidewire since the diminished flexibility may limit the ability of the catheter to conform to the travel path defined by the guidewire, leading to blood vessel trauma. Nonetheless, such catheters carrying ring electrodes are in favor because of the high level of reliability of the electrical connections therein.

The conventional processes for forming ring or metal band electrodes flush with the outer surface of a catheter are arduous, time-consuming and/or require further processing. For example, in one process, metal bands and sleeves therebetween are slipped over the tubing outer surface with the sleeves maintaining the appropriate spacing between adjacent electrodes; this requires the use of additional pieces (namely, the sleeves) and an arduous assembly process. Another process requires the tubing to be stretched to lower the outer diameter thereof, metal bands placed over the stretched tubing and disposed in appropriate spatial relationship, and the tubing then heated and released. The metal bands sink into the heat-softened tubing outer surface as the tubing resumes its original configuration (except where the metal bands are embedded therein). This technique requires additional stretching, heating and cooling steps.

The ring electrodes are commonly 0.040 or 0.080 inch in width and composed of the relatively expensive materials gold or platinum. Where a single catheter contains several ring electrodes, clearly the catheter is a relatively expensive device. Further, any placement of a large number of ring electrodes on the catheter results in a catheter which is stiff and difficult to place, thereby presenting an increased risk of blood vessel perforation. As there is but a single layer of wound wires extending from the proximal end of the catheter to the several ring electrodes, the number of ring electrodes borne by a catheter is strictly limited to 6 or so.

Accordingly, it is an object of the present invention to provide an electrode-carrying catheter which does not utilize ring electrodes.

Another object is to provide in one embodiment such a catheter which provides a large number of side electrodes economically and without stiffening.

A further object is to provide such a catheter which in one embodiment has layers of embedded wound wires.

It is also an object of the present invention to provide such a catheter which is easily and inexpensively manufactured.

It is another object to provide processes for the manufacture of such catheters.

SUMMARY OF THE INVENTION

It has now been found that the above and related objects of the present invention are obtained in an electrode-carrying catheter (without ring electrodes) of low cost and high reliability, comprising elongate flexible tubing defining a proximal end, a distal end, and an electrically insulative outer tubular layer intermediate the ends. The tubing includes a flexible, optionally electrically conductive, core of wire and a flexible non-conductive core-covering layer of plastic about the core. At least one electrically conductive electrode is disposed at least partially on the outer tubular surface. Conducting means are provided for conducting electrical signals between the proximal end and each of the electrodes. The conducting means includes, intermediate the core and the outer tubular layer, a longitudinally-spaced plurality of flexible electrically conductive wires helically wound around and at least partially into the core-covering layer and insulated from one another at least by the core-covering layer and from the environment at least by the outer tubular layer. The outer tubular layer, the core-covering layer and any electrical insulation about the wound wires define a removed section about a segment of each of the electrodes to enable electrical contact between a respective one of the wound wires and a respective one of the electrodes. Each of the electrodes is in the form of an electrically conductive flexible flat means for providing electrical communication with a respective one of the wound wires. Each of the flat means is electrically and physically joined to a respective one of the wound wires, and wrapped about and crimped onto the outer tubular layer.

Preferably, the core is a stranded configuration of stress-relieved stainless steel wire having an appreciable torsional strength and a slow return after lateral bending. The core-covering layer and the outer tubular layer are formed of polyurethane. At least during the wire winding step, the core-covering layer is softer than the outer tubular layer. The core-covering layer is over-extruded over the core, and the outer tubular layer is over-extruded over the wound wires and the core-covering layer. Where each of the wound wires is covered with electrical insulation, the electrical insulation covering each wound wire defines a removed section beneath one of the electrodes.

The preferred flat means is a flat copper ribbon having a pair of opposed ends, the ribbon being electrically and physically joined at one end to a respective one of the wound wires (at its exposed portion), wrapped under tension completely about the outer tubular layer, and physically joined at the other end to itself. The ribbon is preferably joined to the wound wires by welding.

Preferably each ribbon is crimped onto the outer tubular layer at least 24 crimp points. The removed sections are filled with an elastically insulative adhesive such as epoxy.

Where the core is electrically conductive and has an extension projecting distally from the distal end, an electrically conductive end electrode is crimped distally onto the core extension and is proximally crimped onto and radially flush with the outer tubular layer.

In a preferred embodiment, the core-covering layer defines at least an inner annulus and a co-axial outer annulus disposed radially outwardly of the inner annulus, and the plurality of wound wires defines an inner set of wound wires helically wound in one direction within the inner annulus and an outer set of wound wires helically wound in the opposite direction and disposed radially outwardly of the inner set. The plurality of electrodes (i.e., the ribbons) defines at least a proximal set of electrodes and a distal set of electrodes, the proximal set of electrodes and outer set of wound wires in the outer annulus being in electrical communication, and the distal set of electrodes and the inner set of wound wires in the inner annulus being in electrical communication.

The catheter preferably contains at least ten of the electrodes and is substantially flexible.

The present invention also encompasses a process for manufacturing an electrode-carrying catheter of high reliability, comprising the step of over-extruding a core-covering layer of plastic over a flexible, optionally electrically conductive, elongate core of wire. A spaced apart plurality of flexible, electrically conductive wires is helically wound about and at least partially into the soft outer layer. A flexible, non-conducting outer layer of plastic is over-extruded over the wound wires and the core-covering layer. Portions of the outer layer, the core-covering layer and any insulation about the wound wires are removed at a plurality of spaced locations so as to expose a portion of each of the wound wires. The removed portions at each location are replaced with an electrically conductive, flexible, flat ribbon electrically and physically joined at one end to a respective one of the wound wires (at its exposed portion), wound under tension completely about the outer layer and physically joined at the other end to itself. The ribbon is then crimped onto the outer layer at each spaced location.

In a preferred embodiment, the soft outer layer defines at least an inner annulus and a co-axial outer annulus deposed radially outwardly of the inner annulus. The plurality of wound wires defines an inner set of wound wires helically wound in one direction within the inner annulus and an outer set of wound wires helically wound in the opposite direction and disposed radially outwardly of the inner set. The plurality of ribbon electrodes defines at least a proximal set of ribbon electrodes and a distal set of ribbon electrodes, the proximal set of ribbon electrodes and the outer set of wound wires in the outer annulus being in electrical communication and the distal set of ribbon electrodes and the inner set of wound wires in the inner annulus being in electrical communication. The removed portions are filled with an electrically insulative adhesive such as epoxy.

BRIEF DESCRIPTION OF THE DRAWING

The above and related objects, features, and advantages of the present invention will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

Figure 1:
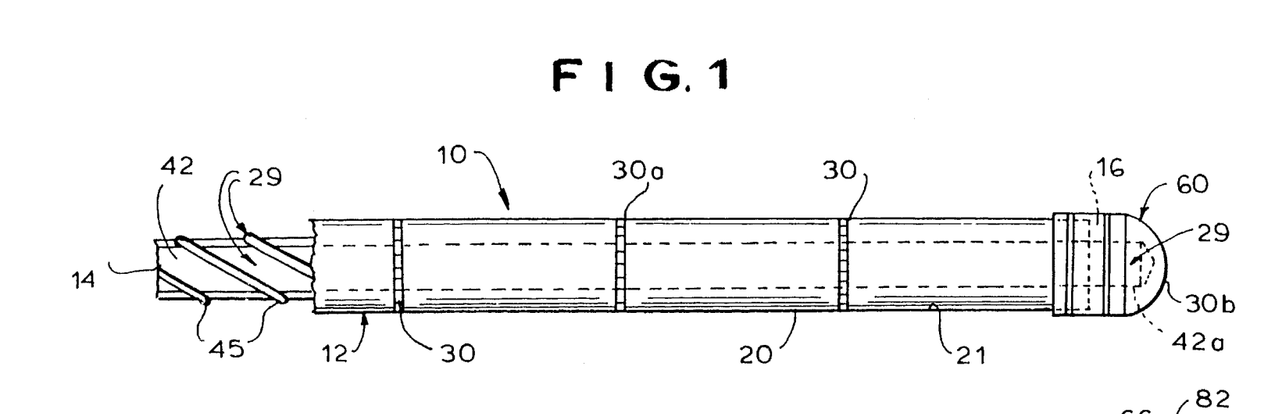
FIG. 1 is a fragmentary side elevational view of an electrode-bearing catheter according to a preferred embodiment of the present invention, with three side electrodes and one end electrode.

Referring now to FIG. 1, therein illustrated is an electrode-carrying catheter according to the present invention, generally designated by the reference numeral 10. While the configuration and dimensions of the catheter will vary with the intended application for the catheter, it is generally of the same overall width and length of the known catheters for the same application. The catheter 10 is formed of elongate, flexible tubing generally designated 12. The tubing 12 defines a proximal end 14, a distal end 16, and a sidewall or outer tubular layer 20 connecting the ends 14, 16 and having an electrically insulative outer surface 21.

Figure 2:
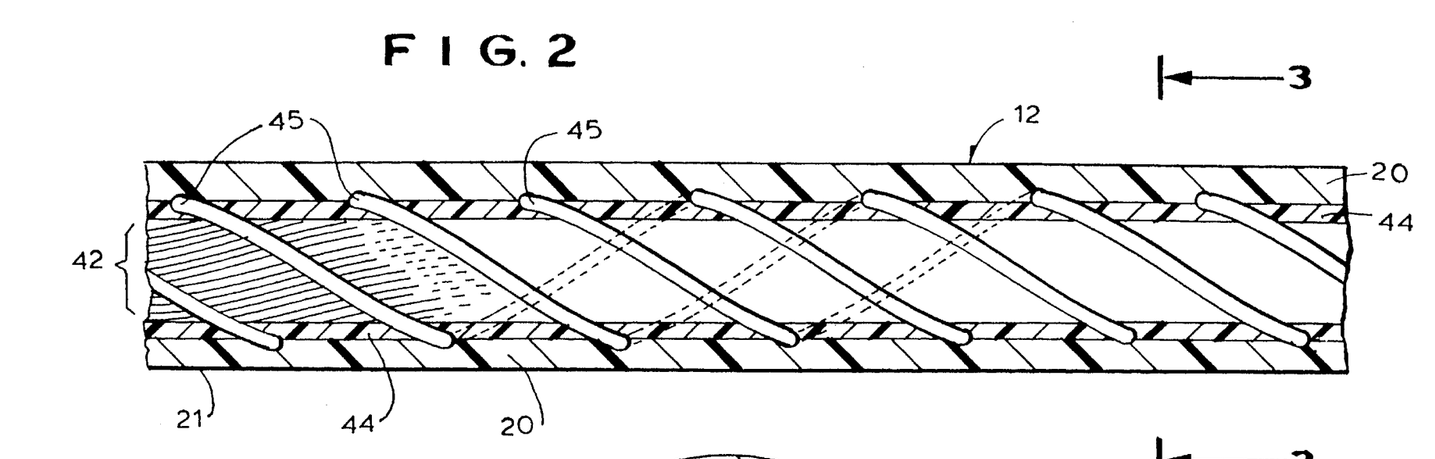
FIG. 2 is a fragmentary side elevational view of the tubing and wound wires thereof, partially in section and to a slightly enlarged scale.
Figure 3:
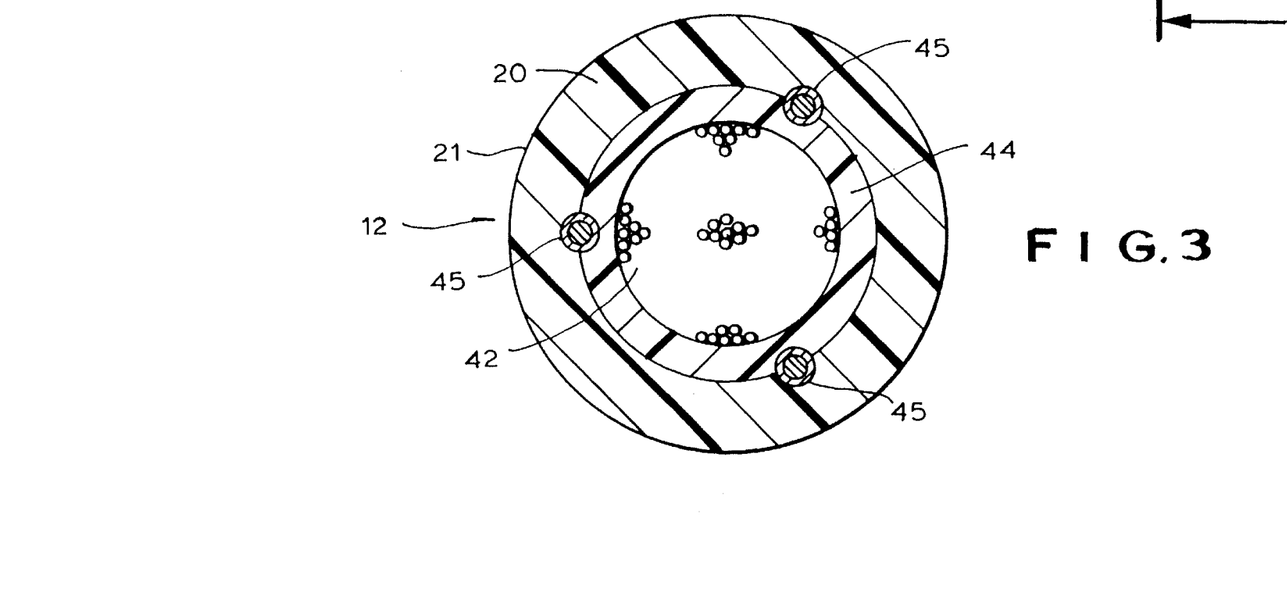
FIG. 3 is a fragmentary sectional view taken along the line 3—3 of FIG. 2, to a greatly enlarged scale.

Referring now to FIGS. 2–4 as well, at least one electrode 30 is disposed on the tubing 12. The electrode may be a side electrode 30a disposed on the outer surface 21 (three side electrodes being illustrated in FIG. 1), an end electrode 30b disposed on the distal or front end 16 (one end electrode being illustrated in FIG. 1), or a combination thereof. The side electrodes 30a extend predominantly transversely (i.e., circumferentially) relative to the tubing axis. Preferably the side electrodes 30a extend fully around the circumference of the tubing 12, and the end electrode 30b extends over the full diameter of the distal end 16 (as illustrated). Conducting means, generally designated 29, are provided for conducting electrical signals between the proximal end 14 and each of the electrodes 30a, 30a, 30a, 30b.

Referring now to FIGS. 2 and 3, the tubing 12 is composed initially of a flexible, conductive core 42 and a flexible, insulating, core-covering layer 44 disposed over the outer surface of the core 42. If there is an electrode 30b, the core 42 must be electrically conductive. In any case, the core 42 is preferably formed of a wire exhibiting an appreciable degree of torsional stiffness (so that rotation of the proximal end 14 of the tubing is transmitted to the distal end 16) and a slow return or recovery after a lateral bending (so that the catheter makes good contact along its length with the walls of the vessel into which it is inserted). A preferred core 42 is a 0.032 inch outer diameter length of a stranded and twisted configuration of stress-relieved wire, such as 304 stainless steel 7×19. (The stress-relieving process involves heating the stainless steel wire—e.g., to 1,200° F., a temperature below the annealing temperature—so that it tends to retain its stress-relieved configuration.)

The core-covering layer 44 may be formed by over-extruding (or otherwise forming) a plastic over the core 42. A preferred soft core-covering layer 44 is formed of a soft plastic such as polyurethane having a durometer hardness of 80A available under the trade name Tecoflex (from Thermedics Inc. of Woburn, Mass.). A preferred hard core-covering layer 44 is formed of a hard plastic such as polyurethane having a Shore durometer hardness of 75D available under the trade name Tecothane (also from Thermedics Inc.). The core-covering layer 44 is preferably formed of an opaque plastic to facilitate viewing of the wires 45, by providing contrast.

As part of the conducting means, flexible, insulated, electrically conductive wires 45 (three wires 45 being shown, one for each side electrode 30a) are helically or spirally wound around and at least partially into the core-covering layer 44 about the core 42. The wound wires 45 are longitudinally spaced apart in a single layer such that each of the wires 45 is insulated from the two adjacent wires 45 by portions of the core-covering layer 44 as well as the wire insulation, In order to preclude accidental movement of the spaced apart plurality of wound wires 45 prior to over-extrusion of outer layer 20 thereover, the wires 45 are helically or spirally wound around the layer 44 (under roughly hand tension) so that they at least partially embed themselves within the core-covering layer 44 (preferably at least 75% of the diameter becoming embedded). The wound wires 45 are preferably insulated magnet wires having a gauge of 34. As the core-covering layer 44 ensures electrical separation between the various wires 45, the wires are not insulated in order to prevent shorting if they come into contact, but merely to facilitate subsequent processing steps. Indeed, uninsulated wires may be used if desired. It will be appreciated that, while only three wires 45 have been illustrated, the number of wires 45 can be varied as desired for particular applications depending on the number of side electrodes 30a. Each wire 45 (or the insulation thereon) is preferably of a different color so that the various wires in and about the core-covering layer 44 can be distinguished.

Where the core-covering layer 44 is formed of a soft plastic (e.g., Shore A hardness of 80), the hand tension exerted on the wires 45 during the winding step are sufficient to at least partially embed the wires 44 into the core-covering layer 44 (at least about 75% of the cross section of the wires being embedded). Where the core-covering layer 44 is formed of a hard plastic (e.g., Shore D hardness of 75), the core-covering layer 44 is preferably heated (e.g., by hot air guns) at the point where the wire contacts the layer 44, thereby to temporarily decrease the hardness of the hard plastic and allow the wire 45 to become embedded therein under simple hand tension. The use of a hard plastic for the core-covering layer 44 is preferred because, once cooled, it better immobilizes the wires 45 and because it contributes to the torsional stiffness of the catheter 10. Typically, heating of the hard plastic to about 200° F. provides sufficient temporary softening of the plastic to enable the wires 45 to become embedded all the way into the core-covering layer 44.

Finally, a flexible, thin insulating layer of plastic is over-extruded (or otherwise formed) over the core-covering layer 44 and any exposed portion of wound wires 45 to form the outer tubular layer 20 of the tubing 12 defining outer surface 21. Thus the conductive wires 45 are isolated from one other and the environment by means of the core 42, the core-covering layer 44, and the outer layer 20 as well as any insulation on the wires. The outer tubular layer 20 may be formed of polyurethane or any of the other flexible, electrically insulative plastics commonly used in catheter construction such as polyvinyl chlorides, polyesters and various copolymers.

Where the core-covering layer 44 is formed of soft plastic, the outer hard layer 20 is preferably formed of polyurethane having a Shore D hardness of 71–75 available under the trade name Tecothane (from Thermedics Inc.). Where the core-covering layer is formed of hard plastic, the outer layer 20 is preferably formed of polyurethane having a Shore D hardness D of 63 available under the trade name Pebax (from Elf Atochem of Birdsboro, Pa.). Thus it will be appreciated that, when the core-covering layer 44 is formed of soft plastic, it may in the final product be softer than the outer layer 20, but that, when it is formed of hard plastic, it may in the final product be harder than the outer layer 20. This is true even though, during the winding process, the pertinent portions of the core-covering layer formed of hard plastic are temporarily softened by heating to allow embedding therein of the wires 45.

The outer layer 20 is preferably over-extruded to a thickness slightly greater than that ultimately desired so that it may be subsequently ground down (preferably using a conventional centerless grinding machine) down to a constant outer diameter, thereby masking irregularities originally present due to the presence of the wires 45 wound on the core-covering layer 44.

If the core-covering layer 44 is of sufficient thickness to receive and electrically isolate the wound wires 45 (which must then be totally embedded therein) and is furthermore subsequently treatable (e.g., curable or modifiable) to provide an abrasion-resistant surface, application of the outer layer 20 may be dispensed with entirely and the core-covering layer 44, thus treated after the wires 45 are totally embedded therein, will also serve as the outer layer 20.

Figure 4A:
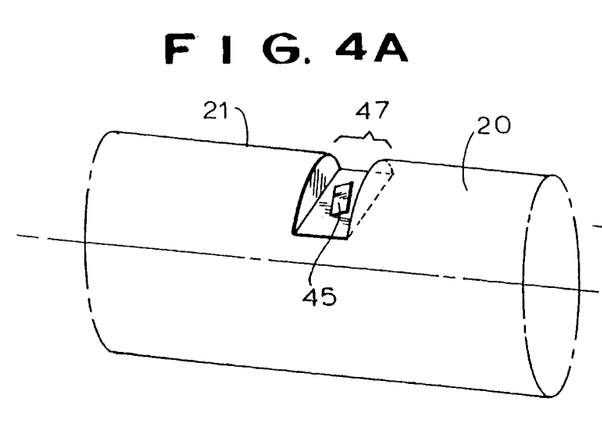
FIGS. 4A—4D are schematics illustrating the process of applying the flat ribbon electrode to the tubing.
Figure 4B:
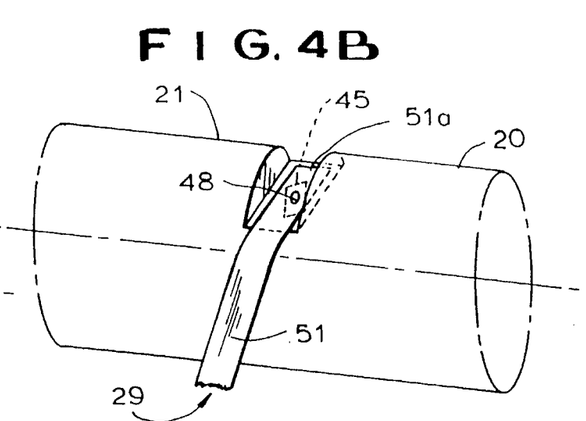

Referring now to FIG. 4A, next, the outer layer 20 and core-covering layer 44 of the tubing 12 are removed at a plurality of spaced locations along its circumferential sidewall 21 (corresponding to the ultimate locations of the ribbon electrodes 51) so as to form windows 47. Each window 47 exposes a portion of a respective one of the wound wires 45 at its respective location. The outer layer 20 and core-covering layer 44 can be removed at the desired locations by various techniques such as cutting, skiving, drilling or grinding, but grinding or cutting is preferred as they are easy, quick and precise operations. The windows are preferably formed using a grinding wheel having a diameter suitable for forming windows of the desired size (such as a 0.020 inch diameter) until the grinding has removed a suitable amount of the two layers 20, 44. Where present, the insulation about each wire 45 is also removed at one location so as to expose the conductive element of the wire 45.

Figure 8:
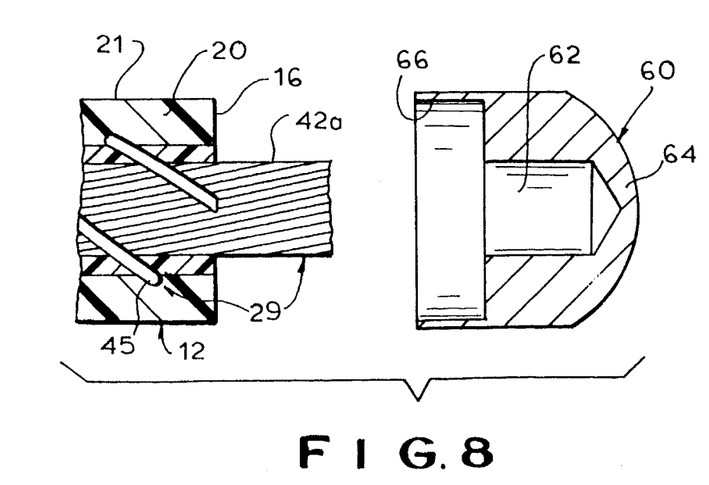
FIG. 8 is a fragmentary exploded side elevational view of the catheter and end electrode assembly.

Referring now to FIG. 8, where there is to be an end electrode 30b as well, in a similar fashion the outer layer 20 and the core-covering layer 44 at the distal end 16 of the tubing 12 are removed (e.g., ground by a grinding wheel) and, where present, the insulation about the end of the core 42 is also removed. Grinding of the distal end 16 continues until there is exposed an appropriate length (about 0.035 inch) of the conductive element of the core wire 42, this exposed conductive element projecting forwardly from the distal end 16 of the tubing 12 as a core extension 42a.

It will also be appreciated that the two layers 20, 44 of the sidewall 21 may have the portions at the particular locations removed therefrom simultaneously to form windows 47. The locations at which the layers 20, 44 are to be removed are predetermined by the desired location of the ribbon electrodes 30a. Before removal of the portions of the layers 20, 44, the wound wires 45 are already in place and in fixed spatial disposition relative to one another. Accordingly, once the location of one wire 45 is determined (perhaps by inspection of the distal end 16 where they are initially visible), then the location of all of the remaining wires 45 is known. Thus, grinding elements of a grinding machine, for example, can be appropriately positioned relative to the known wire, and the desired portions of the layers 20, 44 (and, when present, the wire insulation) simultaneously removed at each location. This enables the windows 47 to be inexpensively formed in a low labor operation.

Figure 4C:
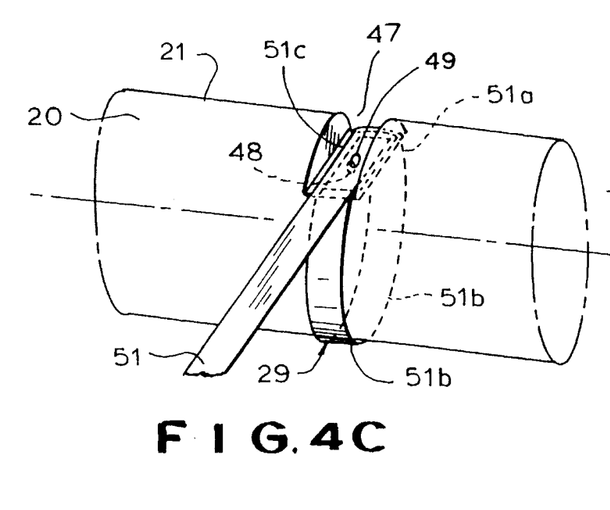
Figure 4D:
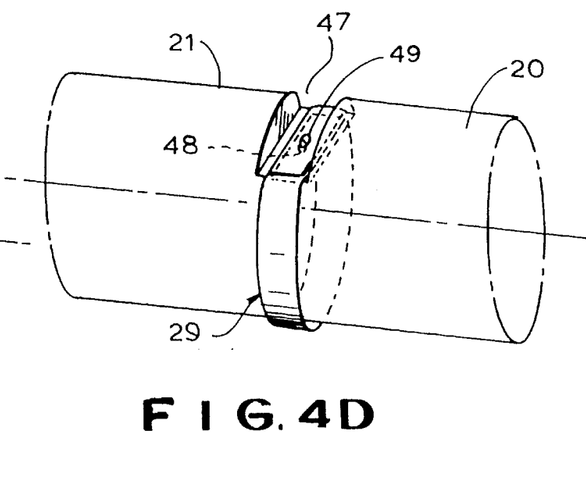

Referring again to FIG. 4B, after creation of the windows 47, a flat conductive element 51, such as a flat copper ribbon (0.001×0.012 inch), is electrically and physically joined to the exposed portion of the wire 45 under the window 47. Preferably the ribbon 51 is welded to the exposed wire 45 at point 48 using a welder such as that available under the trade name Light Force Welder (from Unitek Equipment Inc. of Monrovia, Calif.). Typically, a free ribbon end 51a is first welded to the wire 45. Referring now to FIG. 4C, the ribbon 51 and the tubing 10 are then rotated relative to one another until a shank 51b of the ribbon 51 is wrapped essentially one turn (360°) about the outer layer 20, and back on itself. This may be accomplished by rotating the tubing 12 while using a machine to maintain hand tension on the ribbon 51. Next, the as yet unwelded ribbon end 51c of the loop thus formed is welded to the ribbon 51 at point 49 (preferably at the already welded ribbon end 51a). Finally, as seen in FIG. 4D, the ribbon 51 is removed from the ribbon spool (not shown), e.g., by simply applying a quick tug to the ribbon.

While there is an overlap of the ribbon 51c upon itself 51a, the extra thickness of the additional ribbon layer is of no consequence since even the doubled ribbon is thin relative to the depth of the window 47. It will be appreciated that the ribbon performs the role of an electrode, bringing the signal from the exposed wire (which is located below the hard layer 20) up to the top of the outer tubular layer 20—i.e., up to the catheter outer surface. Preferably the welding equipment uses the electrodes available under the trade name Unitip 111L (available from Unitek Equipment Inc.) or a similar microelectrode which permits the welding equipment to resistively weld the exposed wire 45 and the ribbon 51 together within the confines of window 47.

The application of a ribbon 51 to a wire 45 is then repeated for each of the remaining windows 47.

Figure 5:
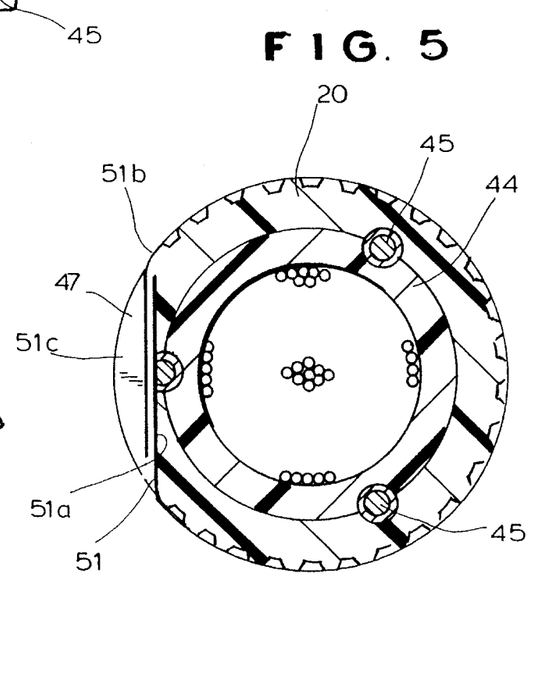
FIG. 5 is a transverse sectional view, to an enlarged scale, of the catheter after crimping of the ribbon electrodes thereon, with the crimps being greatly exaggerated for expository purposes.

Referring now to FIG. 5, a crimping machine (not shown) is then employed to crimp the outer diameter of the ribbons 51 for the most park down to the outer diameter of the tubing 12 (i.e., the outer layer 20). To this end, the crimping machine is provided with a circumferentially spaced plurality of crimping points (for example, 12 points equidistantly spaced about a circumference) which simultaneously crimp and collapse the band of ribbon body 51b to a preset diameter (e.g., 0.078 inch) so that the crimped or collapsed band retains its original circular configuration (except for the end portions in window 47) but with a reduced diameter. Preferably the crimping machine and the catheter workpiece are then relatively rotated (e.g., 15°) and crimping is performed a second time (thus making, for example, 24 equidistantly spaced crimp points), thereby to flatten out any high spots left by the first crimping.

It will be appreciated that, because the crimping operation squeezes the ribbon bodies 51b flush with the tubing outer surface 21, an extremely smooth tubing/ribbon interface is obtained (except for windows 47) without increasing the diameter of the tubing 12. Typically no subsequent hand smoothing of the exterior surface of the tubing at the tubing/electrode interface is required. Accordingly, the present invention employs a crimping process which offers a significant cost advantage over conventional processes for producing a catheter with a flush outer surface by sharply reducing labor requirements and simplifying assembly. To facilitate the crimping process, the plastic of the outer layer 20 may be heated slightly (to about 200° F.) to soften the same and facilitate crimping of the ribbon into the plastic.

While crimping of the side ribbons 51 on the tubing 12 suffices to electrically and physically secure the ribbons 51 to the outer tubular layer 20, excessive bending of the catheter during use may still result in a separation of elements enabling movement of the ribbon 51 relative to the wire 45. Accordingly, for extra security the ribbon 51 may be welded to the wire 45. The welding may be performed using a conventional resistive welder with two electrodes which have been machined to the diameter of the ribbon 51 so that the welder cannot damage the same under the pressure of the weld. A preferred resistive welder is available under the trade name Thin Line Welder (from Unitek Equipment Inc.).

As a highly-desirable by-product of the welding process, when used, the heat generated thereby melts the outer layer 20 underneath and about the circumferentially-extending ribbon body 51b, allowing it to reform and securely attach itself to the ribbon body 51b. Accordingly, the ribbon 51 adheres better to the outer layer 20 and is less likely to separate therefrom during subsequent flexure of the catheter, thus enhancing reliability of the product. Nonetheless this welding step is generally unnecessary where the crimping operation described above and the adhesive operation described below are properly performed.

Figure 6:
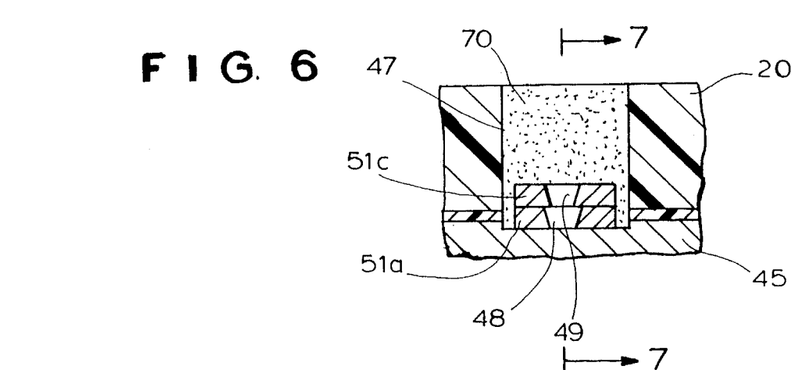
FIGS. 6 and 7 are fragmentary longitudinal and transverse sectional views, respectively, of the catheter after the addition of adhesive, to a greatly enlarged scale.
Figure 7:
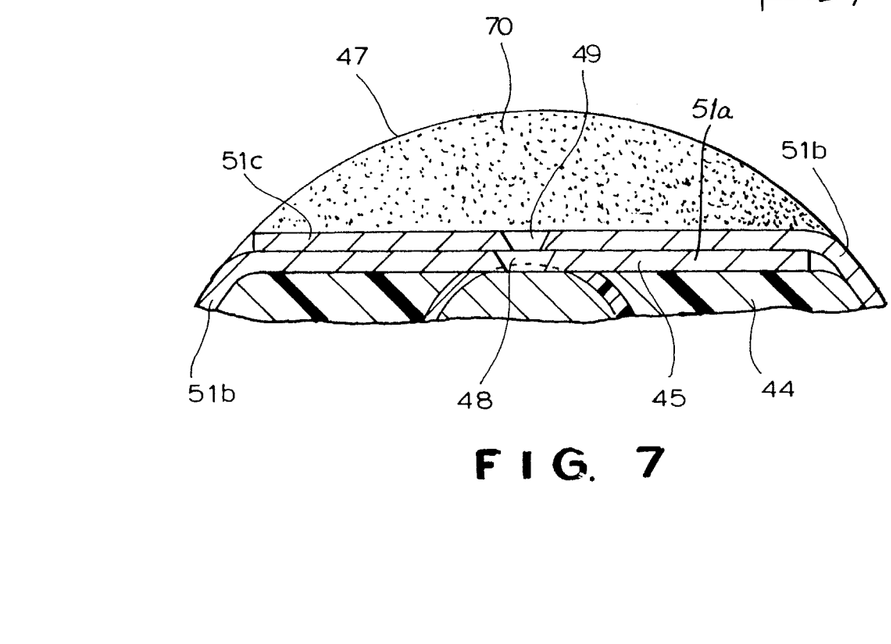

As indicated above, the crimping operation results in a catheter having a smooth outer surface except for the window 47. Because the ribbon ends 51a, 51c are disposed within the window 47, they are not crimped by the crimping operation and thus do not receive the extra measure of security which would be the result if they were crimped together and onto the exposed wire portion. Accordingly, referring now to FIGS. 6 and 7, it has been found desirable to fill in the remaining portion of each window 47 (that is, the portion not occupied by the ribbon ends 51a, 51c and the welds 48, 49) with an electrically insulative adhesive 70 such as epoxy or cyanoacrylate. The adhesive further stabilizes the ribbon ends 51a, 51c against movement or breaking away from the exposed portion of wire 45 by protecting it from outside forces (that is, forces outside of the outer tubular layer 20) and positively securing it to both the outer tubular layer 20 and the exposed portion of the wire 45. The adhesive may be clear so that the welds 48, 49 may be viewed. The quantity and surface tension of the adhesive prior to cure are preferably selected such that, when the window 47 is filled with a known quantity of the adhesive, the upper surface of the cured adhesive conforms generally to the outer surface 21 of the upper tubular layer 20, thereby avoiding any need for subsequent hand smoothing of the exterior surface of the tubing/adhesive interface. Epoxy having 100% solids is preferred as it retains its shape during cure. The presence of the adhesive within the window 47 ensures that the ribbon ends 51a, 51c do not become loose.

The manufacturing process of the present invention is in all its aspects easy and inexpensive relative to the labor-intensive nature of most other manufacturing processes for producing an electrode-carrying catheter, while affording a product of enhanced reliability.

Figure 9:
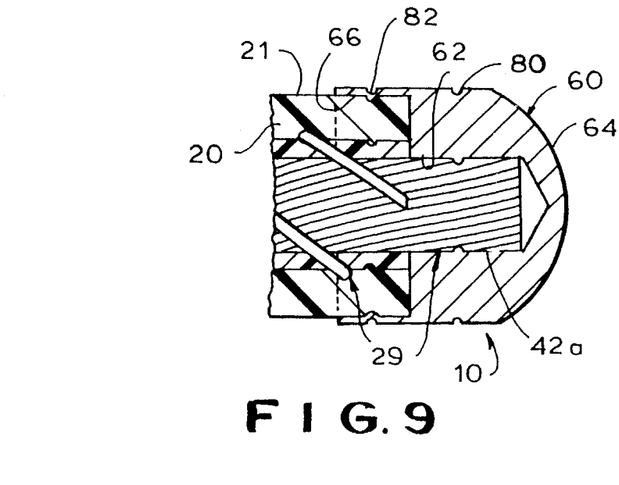
FIG. 9 is a fragmentary side elevational view of the assembly of FIG. 8 after crimping, with the crimps being greatly exaggerated for expository purposes.

Referring now to FIG. 8, where the catheter 10 includes at least one end electrode 30b as one of the electrodes 30 thereof, the electrically conductive end electrode is preferably configured and dimensioned as a flexible cap, generally designated 60, disposed across the distal end 16 of the tubing 12 in order to close the same. The cap 60 may be formed of the same material as the ribbon 51 or a different material. The cap 60 is of appreciable thickness and has a head 64 defining a recess 62 on its proximal surface and a proximally projecting circumferential band 66. As cap 60 is slipped over the distal end, the core extension 42a is received within cap recess 62, and the distal end of the outer layer 20 is received within the cap band 66. Referring now to FIG. 9, the head or cap distal end 64 is then crimped onto the core extension 42a, at 80, and the band or cap proximal end 66 is crimped onto and flush with the outer layer 20, at 82. This double crimping 80, 82, using a crimping machine as described hereinabove in connection with the crimping of the ribbons 51, securely joins the end electrode 30b with the core extension 42a and hard layer 20, neither a ribbon 51 nor a welding step being required.

The present invention reduces both the cost of materials and the cost of production. As there is no necessity for the use of the standard 0.040 or 0.080 inch wide electrodes made of gold or platinum, the cost of materials is substantially diminished relative to the use of platinum or gold ring electrodes. Also, the labor cost involved in manufacturing the catheter is also decreased as the laborious and time-consuming step of threading the ring electrodes onto the tubing is no longer necessary.

Additionally, because the ribbon electrode is only about 0.015 inch wide, the catheter of the present invention has an extremely small proportion of metal on its surface relative to a like catheter with a like number of conventional electrodes on the surface thereof. As a result, the catheter maintains its flexibility even when a large number of ribbon electrodes are mounted thereon. Typically, conventional catheters with six or more ring electrodes are stiff, difficult to place, and involve increased risk of patient perforation. The present invention permits ten or more ribbon electrodes to be disposed on a still flexible catheter.

Figures 10, 11, 12:
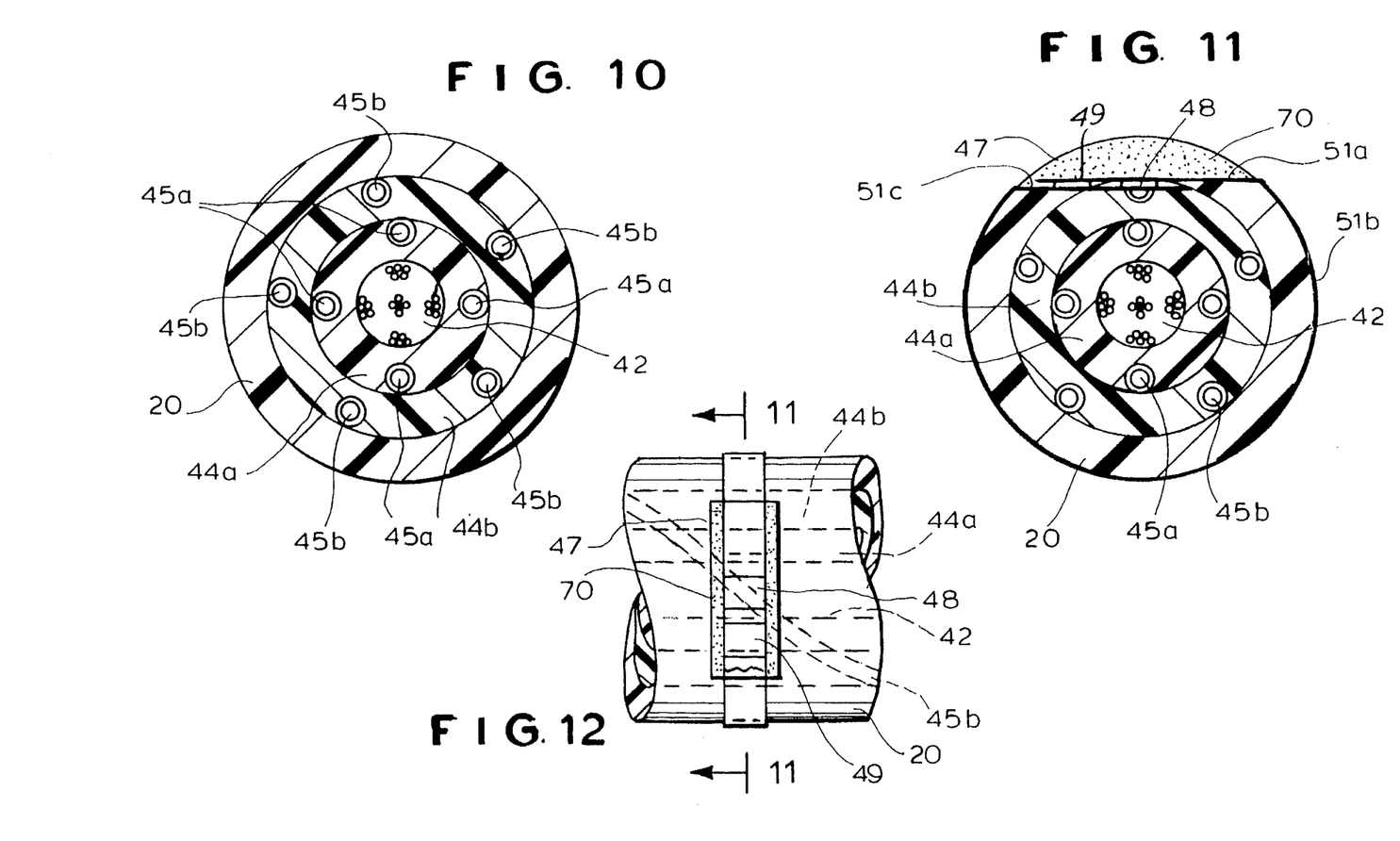
FIG. 10 is a transverse sectional view of a preferred embodiment of the catheter with two wire layers before window formation.
FIG. 11 is a transverse sectional view thereof after application of a ribbon electrode, but before crimping.
FIG. 12 is a fragmentary sectional view taken along the line 12—12 of FIG. 11.

In order to enable the deployment of almost twice the number of electrodes (ten or more instead of six) in the same size catheter, the wound wires are preferably embedded in multiple layers within the core-covering layer 44 of the catheter body rather than just one layer. Referring now to FIGS. 10–12, therein illustrated is a multiple layer embodiment of the present invention. In this embodiment, the core-covering layer 44 defines at least an inner annulus 44a and a co-axial outer annulus 44b disposed radially outwardly of the inner annulus 44a. Similarly, the plurality of wound wires 45 defines an inner set of wound wires 45a helically wound in one direction within the inner annulus, and an outer set of wound wires 45b helically wound in the opposite direction and disposed radially outwardly of the inner set 45a. The plurality of ribbon electrodes 51 defines at least a proximal set of the electrodes and a distal set of the electrodes. The proximal set of electrodes and the outer set of wound wires 45b in the outer annulus 44b are in electrical communication, while the distal set of ribbon electrodes and the inner set of wound wires 45a in the inner annulus 44a are in electrical communication.

To eliminate confusion among the layers of wire, the different wire layers are preferably helically wrapped in opposite directions—one layer clockwise helically and the other layer counterclockwise helically. Preferably the proximal set of electrodes and the outer set of wound wires 45b in the outer annulus 44b are electrically connected first, while the distal set of electrodes and the inner set of wound wires 45a in the inner annulus 44a are electrically connected subsequently. This enables the outer set of wound wires 45b to be cut, as necessary, to facilitate connecting of the inner set of wound wires 45a and the distal set of electrodes without affecting the previously made electrical connections with the proximal set of electrodes.

Referring now to FIG. 10, in the manufacture of the preferred embodiment having two wire layers with a total of nine wound wires, a flexible, electrically conductive core 42 of stranded 7×19 stainless steel wire (0.018 inch diameter) is over-extruded with a soft, flexible, non-conductive core-covering opaque inner polyurethane jacket 44a (0.038 inch diameter and a Shore D hardness of 75). Four wires 45a are then spiral wrapped in the clockwise direction under tension so that they become at least partially and preferably totally embedded in the inner urethane jacket 44. A soft, flexible, non-conductive core-covering clear polyurethane jacket 44b (0.058 inch diameter and a Shore D hardness of 75) is then extruded over the wire-wrapped inner annulus, including jacket 44a and wires 45a, so as to allow the inner set of wires of 45a to be seen therethrough. Then five wires 45b are spirally wrapped in the counterclockwise direction under tension onto the outer urethane jacket 44b so that they become at least partially and preferably totally embedded in the outer jacket 44b. A transparent or translucent, electrically insulative outer tubular layer 20 (0.078 inch diameter) of plastic is extruded over the wire-wrapped outer annulus 44b, 45b. The resultant structure is illustrated in FIG. 10. It will be appreciated that the opaque inner jacket 44a provides a dark background against which the wires 45b in the clear outer jacket 44b may be discerned.

If desired, at this point the end electrode 30b may be formed by stripping the distal end of the catheter down to the core 42 and allowing about a short length (0.042 inch) of stranded cable 42 to protrude distally as the extension 42a. A gold-plated brass tip electrode 60 is then double crimped onto the core extension 42a.

Returning now to the side electrodes 30a, the outer tubular layer 20 and portions of the outer annulus 44b (and any insulation about the exposed portions of wires 45b are ground or cut away at the proximal end portion of the tubing 12 to form a window 47 and expose a portion of each of the outer set of wound wires 45b in the outer annulus 44b. Once the appropriate windows 47 are formed, the end 51a of each gold-plated ribbon 51 is secured at 48 to the exposed portion of a respective wound wire 45b, then the ribbon body 51b is wrapped under tension circumferentially around the outer tubular layer 20, and finally the other ribbon end 51c is secured to the first ribbon end 51a at 49, all as illustrated in FIG. 4A–4D. Then the inner set of wound wires 45a disposed in the inner annulus 44a are exposed through new windows 47 by grinding or cutting portions of both the outer and inner annuluses 44b, 44a (and any insulation about the exposed portion of wires 45a at the distal end portion of the tubing 12). Each ribbon 51 is then attached to an exposed portion of a respective wound wire 45a in the inner annulus 44b, wrapped around the outer tubular layer 20 and finally fastened onto itself. This completes the initial electrode connections of the catheter.

The ribbons 51 on the outer tubular layer 20 (and in particular the bodies 51b thereof) are double crimped flush with the outer tubular layer 20 using a 12 point crimper, either with or without heating of outer layer 20. Epoxy 70 is then used to fill in the windows 47 and thereby also further secure the ribbon ends 51a and 51c to the outer tubular layer 20, the appropriate annulus 44a or 44b, and the exposed portions of wound wires 45a or 45b. This is the structure illustrated in FIG. 11. The proximal ends of the wound wires 45 are secured using conventional contacting techniques.

As used herein, the terms "insulating", "insulative", "non-conducting" and "non-conductive" are synonyms.

To summarize, the present invention provides an electrode-carrying catheter (without ring electrodes) of high reliability and low cost, the catheter being capable of mounting a large number of side electrodes economically and without stiffening. In one preferred embodiment, the catheter employs layers of wires to provide electrical contact between an electrode and the proximal end of the electrode. The catheter is easily and inexpensively manufactured. The present invention also provides processes for the manufacture of such a catheter.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

I claim:

1. A process for manufacturing an electrode-carrying catheter, comprising the steps of:

(A) over-extruding a core-covering layer of plastic over a flexible, elongate core;

(B) helically winding a spaced apart plurality of flexible, electrically conductive wires about and at least partially into the core-covering layer;

(C) over-extruding a flexible, non-conducting outer layer of plastic over the wound wires and the core-covering layer;

(D) removing portions of the outer layer, the core-covering layer and any insulation about the wound wires at a plurality of spaced locations so as to expose a portion of each of the wound wires;

(E) replacing the removed portions at each location with an electrically conductive flexible ribbon electrode electrically and physically joined at one end to a respective one of the wound wires, wound under tension completely about the outer layer and then joined at the other end to itself; and (F) crimping each of the ribbon electrodes onto the outer layer thereabout at each spaced location.

2. The process of claim 1 wherein the ribbon electrodes are joined to the exposed portions by welding.

3. The process of claim 1 wherein the core-covering layer is softer than the outer layer during the helical winding step.

4. The process of claim 1 including the additional step of heating the portion of the core-covering layer on which the wires are being wound during the winding step.

5. The process of claim 4 wherein the core-covering layer is harder than the outer layer after manufacturing is completed.

6. The process of claim 1 wherein each ribbon electrode has a pair of opposed ends, the ribbon electrode being electrically and physically joined at one end to a respective one of the wound wires, wrapped under tension completely about the outer layer, and physically joined at the other end to itself.

7. The process of claim 1 wherein the core is a stranded configuration of stress-relieved stainless steel wire having an appreciable torsional strength and a slow return after lateral bending.

8. The process of claim 1 wherein the core-covering layer and the outer layer are formed of polyurethane.

9. The process of claim 1 wherein each of the wound wires is covered with electrical insulation and the electrical insulation defines a removed portion beneath a segment of each of the ribbon electrodes.

10. The process of claim 1 wherein the core-covering layer defines at least an inner annulus and a co-axial outer annulus deposed radially outwardly of the inner annulus, the plurality of wound wires defines an inner set of wound wires helically wound in one direction within the inner annulus and an outer set of wound wires helically wound in the opposite direction disposed radially outwardly of the inner set.

11. The process of claim 10 wherein the plurality of ribbon electrodes defines at least a proximal set of ribbon electrodes and a distal set of ribbon electrodes, the proximal set of ribbon electrodes and the outer set of wound wires in the outer annulus being in electrical communication and the distal set of ribbon electrodes and the inner set of wound wires in the inner annulus being in electrical communication.

12. The process of claim 10 wherein the inner annulus is non-transparent and the outer annulus is transparent.

13. The process of claim 1 wherein the outer layer is heated during the crimping step to soften the same.

14. The process of claim 1 which contains at least ten of the ribbon electrodes and is substantially flexible.

15. The process of claim 1 wherein, after crimping, the removed portion at each location is filled with electrically insulative adhesive.

16. A process for manufacturing an electrode-carrying catheter, comprising the steps of:

(A) over-extruding a core-covering layer of plastic over a flexible, electrically conductive, elongate core of wire, the core being a stranded and twisted configuration of stress-relieved stainless steel wire having an appreciable torsional strength and a slow return after lateral bending, the core-covering layer defining at least an inner annulus and a coaxial outer annulus disposed radially outwardly of the inner annulus;

(B) helically winding a spaced apart plurality of flexible, electrically conductive wires about and at least partially into the core-covering layer, a plurality of the wound wires defining at least an inner set of wound wires helically wound in one direction within the inner annulus and an outer set of wound wires helically wound in the opposite direction and disposed radially outwardly of the inner set;

(C) over-extruding a flexible, non-conducting outer layer of plastic over the wound wires and the core-covering layer, the core-covering layer during the winding step being softer than the outer layer;

(D) removing portions of the outer layer, the core-covering layer and any insulation about the wound wires at a plurality of spaced locations so as to expose a portion of each of the wound wires;

(E) replacing the removed portions at each spaced location with an electrically conductive, flexible ribbon electrode having a pair of opposed ends, the ribbon electrode being electrically and physically joined by welding at one end to a respective one of the wound wires, wrapped under tension completely about the outer layer, and physically joined by welding at the other end to itself, the plurality of ribbon electrodes defining at least a proximal set of said ribbon electrodes and a distal set of ribbon electrodes, the proximal set of ribbon electrodes and the outer set of wound wires in the outer annulus being in electrical communication and the distal set of ribbon electrodes and the inner set of wound wires in the inner annulus being in electrical communication;

(F) crimping each of the ribbon electrodes onto the outer layer thereabout at each spaced location; and (G) filling the removed portions with electrically insulative adhesive.

\* \* \* \* \*